United States Patent
Yeh et al.

(10) Patent No.: US 7,098,161 B2
(45) Date of Patent: **\*Aug. 29, 2006**

(54) METHOD OF TREATING ZEOLITE

(75) Inventors: Chen Y. Yeh, Edison, NJ (US);
Xingtao Gao, Edison, NJ (US);
William E. Cormier, Lansdale, PA (US); Gary M. Pasquale, Lansdale, PA (US)

(73) Assignee: ABB Lummus Global Inc., Bloomfield, NJ (US)

( * ) Notice: Subject to any disclaimer, the term of this patent is extended or adjusted under 35 U.S.C. 154(b) by 322 days.

This patent is subject to a terminal disclaimer.

(21) Appl. No.: 10/422,541

(22) Filed: Apr. 24, 2003

(65) Prior Publication Data

US 2004/0014592 A1    Jan. 22, 2004

Related U.S. Application Data

(63) Continuation-in-part of application No. 09/981,926, filed on Oct. 17, 2001, now Pat. No. 6,809,055.

(60) Provisional application No. 60/242,110, filed on Oct. 20, 2000.

(51) Int. Cl.
*B01J 29/06*    (2006.01)

(52) U.S. Cl. .............................. 502/60; 502/64; 502/85

(58) Field of Classification Search ................. 502/64, 502/71, 77, 78, 85
See application file for complete search history.

(56) References Cited

U.S. PATENT DOCUMENTS

| | | | |
|---|---|---|---|
| 3,308,069 A | 3/1967 | Wadlinger et al. | |
| 4,377,502 A * | 3/1983 | Klotz | 502/77 |
| 4,554,145 A * | 11/1985 | Rubin | 423/708 |
| 4,683,214 A * | 7/1987 | Angevine et al. | 502/66 |
| 5,075,269 A * | 12/1991 | Degnan et al. | 502/77 |
| 5,116,794 A | 5/1992 | Skeels et al. | |
| 5,139,759 A | 8/1992 | Cannan et al. | |
| 5,164,169 A | 11/1992 | Rubin | |
| 5,164,170 A | 11/1992 | Rubin | |
| 5,256,392 A | 10/1993 | Shamshoum | |
| 5,258,570 A | 11/1993 | Skeels et al. | |
| 5,393,718 A * | 2/1995 | Skeels et al. | 502/66 |
| 5,427,765 A | 6/1995 | Inoue et al. | |
| 5,457,078 A | 10/1995 | Absil et al. | |
| 5,624,658 A * | 4/1997 | Fitoussi et al. | 423/702 |
| 5,980,859 A | 11/1999 | Gajda et al. | |
| 6,004,527 A | 12/1999 | Murrell et al. | |
| 6,294,150 B1 * | 9/2001 | Takahashi et al. | 423/716 |
| 6,632,767 B1 * | 10/2003 | Huo et al. | 502/64 |
| 6,645,899 B1 * | 11/2003 | Palmery et al. | 502/85 |
| 6,809,055 B1 * | 10/2004 | Overbeek et al. | 502/63 |
| 2002/0055433 A1 * | 5/2002 | Fung et al. | 502/214 |
| 2002/0074263 A1 * | 6/2002 | Shan et al. | 208/134 |
| 2002/0111522 A1 | 8/2002 | Overbeek et al. | |

FOREIGN PATENT DOCUMENTS

WO    WO 01/39882    *  6/2005

\* cited by examiner

*Primary Examiner*—Jonathan Johnson
(74) *Attorney, Agent, or Firm*—Dilworth & Barrese, LLP

(57) ABSTRACT

A method for treating zeolite particles to remove organic templating agent therefrom is accomplished by calcining the zeolite particles in a fluidized-bed at a temperature of no more than about 600° C. for a period of time sufficient to remove at least about 50% of the organic templating agent.

1 Claim, 1 Drawing Sheet

METHOD OF TREATING ZEOLITE

CROSS-REFERENCE TO RELATED APPLICATION(S)

The present application is a continuation-in-part of U.S. application Ser. No. 09/981,926, filed Oct. 17, 2001 and now issued as U.S. Pat. No. 6,809,055 B2, which claims priority to provisional application Ser. No. 60/242,110 filed Oct. 20, 2000 to which priority is claimed herein.

BACKGROUND

1. Technical Field

The present disclosure relates to a method of treating zeolite, and particularly to a method of calcining a zeolite to remove organic templating agent therefrom.

2. Background of the Art

Zeolites and molecular sieves are generally used in a wide variety of catalytic procedures. In general, zeolites and molecular sieves may be prepared by a procedure which involves forming the structure from a reaction mixture that includes silica and alumina, and often with an organic structure directing agent (often referred to as a "template" or "templating agent") such as, but not limiting to linear amines, linear diamines, and quaternary ammonium salts. As an example, such quaternary ammonium salt may be tetraethylammonium hydroxide. The organic structure directing agent can be removed from the resultant zeolite by a heat treatment process, often referred to as "calcination", at an elevated temperature. The acid form of the formed zeolite structure or molecular sieve is then produced by ion exchange, such as, but not limited to, ammonium exchange, followed by further calcination. In some processes, the ammonium exchange step occurs before the calcination, thereby simplifying the sequence of steps. In many cases, the (additional) heat treatment, also referred to as calcination, is executed subsequent to a forming step. In this forming or shaping step, the zeolite or molecular sieve is produced into a shape to allow use in for example fixed bed catalytic operation.

In prior methods of calcining the zeolite is heated in tray calciners or in rotary calciners to remove the templating agent. However, the known methods suffer from drawbacks. In particular, it is possible to develop hot spots of uneven temperature. These hot spots result in a non-uniform organic decomposition and low activity product. Moreover, decomposition or combustion of the organic template can produce water vapor, which results in steaming in certain regions. Steaming can result in localized dealumination of the catalyst, with a change in acid sites and catalyst activity. Such irregularities can adversely affect catalyst performance in certain conversion processes.

In the current art, it has been recognized that the state or characteristics of the zeolite or molecular sieve may be effected by the final heat treatment step. However, it has not been recognized that, in the heat treatment to remove the organic structure directing agent, the performance of the zeolite or molecular sieve is affected significantly by changing the state or characteristics of the zeolite or molecular sieve materials.

U.S. Pat. No. 5,258,570 teaches that the catalytic activity of zeolite beta can be improved by activating the formed zeolite by heating at elevated temperatures of from about 600° C. to 675° C. in order to reduce so-called "strong" acid sites. In accordance with U.S. Pat. No. 5,258,570, zeolite beta produced by conventional procedures is specifically treated to reduce acid sites to thereby increase catalyst activity.

Contrary to what is taught in U.S. Pat. No. 5,258,570, it has surprisingly been found that controlled heat treatment or calcination to remove the organic structure directing agent and exposure of the zeolite or molecular sieve during this treatment to average temperatures preferably below 600° C. is desired to create acid sites of a specific nature and strength. These created acid sites, as can be measured by the temperature controlled desorption of ammonia, are surprisingly found to significantly enhance catalytic performance in reactions, such as, but not limited to, hydrocarbon conversion technologies, and environmental abatement technologies.

What is needed is a method of catalyst preparation which avoids the drawbacks of prior calcining methods in order to achieve better catalyst performance.

SUMMARY OF THE INVENTION

A method is provided herein for treating zeolite particles to remove organic templating agent therefrom. The method comprises calcining the zeolite particles in a fluidized-bed at a temperature of no higher than about 600° C. for a period of time sufficient to remove at least about 50% of the organic templating agent. The method provides a catalyst having superior activity.

BRIEF DESCRIPTION OF THE DRAWINGS

Various embodiments are described herein with reference to the drawings wherein.

DETAILED DESCRIPTION OF PREFERRED EMBODIMENT(S)

Figure 1:
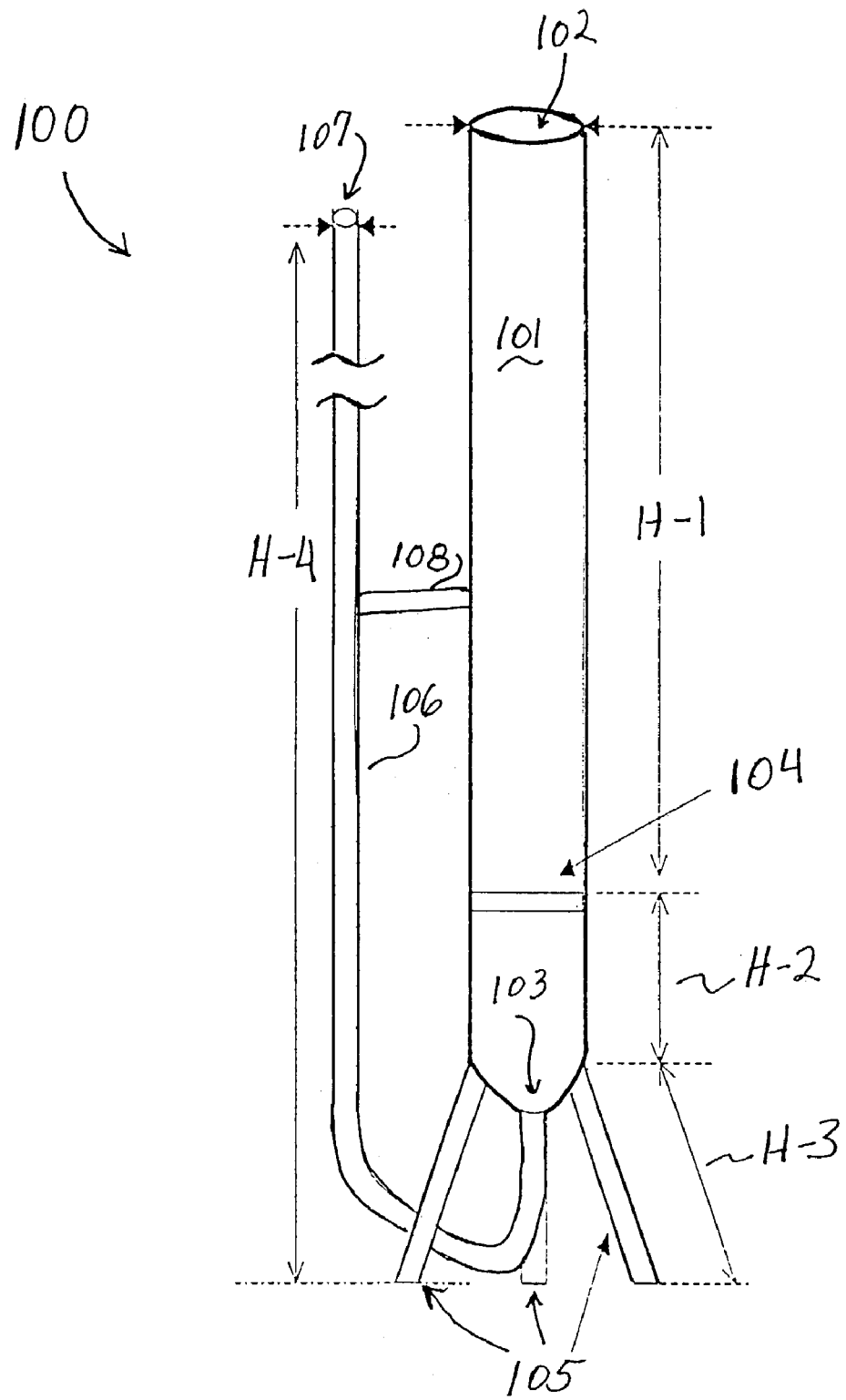
FIG. 1 is a diagrammatic illustration of a fluidized-bed reactor for calcining the catalyst in accordance with the invention.

The present invention employs a fluidized-bed reactor to effect calcining of a zeolite catalyst to remove organic templating agents, or "structure directing agents." As used herein, the term "zeolite" includes molecular sieves.

U.S. patent application Ser. No. 09/981,926, filed Oct. 17, 2001, which is herein incorporated by reference, teaches that the performance of a zeolite is significantly affected by changing the state or characteristics of the zeolite. Controlled heat treatment or calcining to remove the organic templating agent in the zeolite creates acid sites of a specific nature and strength, and an average pore structure of a specific volume and size.

The current working model is that the so-called "strong acid sites" are reduced primarily as a result of a loss of a specific type of tetrahedral aluminum. As a result, in accordance with an aspect of the present invention, in producing a zeolites or molecular sieve, processing conditions that reduce the amount of the specific type of tetrahedral aluminum and thereby reduce the number of strong acid sites should be minimized or avoided in order to provide for improved catalyst activity. As hereinabove indicated, in order to minimize the loss of the specific tetrahedral aluminum and thereby maintain a certain minimum amount of strong acid sites, the conditions at which the templating agent is removed should be controlled so as to reduce and/or eliminate exposure to temperatures above about 600° C. for a prolonged period of time. In addition, in a preferred embodiment steaming should be avoided, for example (but not limited to), by slow heating to the final calcination temperature.

Moreover, processing of the zeolites or molecular sieve after the removal of the templating agent should also be controlled to reduce and/or eliminate exposure to temperatures above about 600° C. For example, the exchange steps and final calcination of the ion exchanged zeolite or molecular sieve should occur at moderate temperatures. Ion exchange includes, but is not limited to, exchange of Na with $NH_4NO_3$ to produce the $NH_4$-form of the zeolite or molecular sieve. In addition, use of organic agents (e.g., to increase physical strength, to facilitate extrudability, etc.) in procedures for extruding the zeolites or molecular sieve into a desired shape or form should also be minimized or avoided.

The prior art did not recognize that strong acid sites in zeolites and molecular sieves increase catalytic activity and that processing conditions for producing zeolites and molecular sieves should be controlled to prevent loss of strong acid sites. In the prior art, processing steps after formation of the zeolites or molecular sieve reduced the number of strong acid sites to values below those of the present invention, and such reduction resulted in a reduction in catalytic activity.

More particularly, in a preferred embodiment the zeolite or molecular sieve is one that contains silica and alumina in a silica to alumina molar ratio of 6:1 or higher or 30:1 or higher that is prepared by use of a templating or organic structure directing agent that includes an organic nitrogen compound. As representative but non-limiting examples of zeolites there may be mentioned: zeolite beta, zeolite L, TEA-mordenite, MCM-22, MCM-36, MCM-39, MCM-41, MCM-48, PSH-3, ZSM-5, Breck-6 (also known as EMT), ZSM-11, ZSM-12, ZSM-22, ZSM-23, ZSM-35, ZSM-48, SSZ-32, TUD-1, etc. A preferred zeolite is zeolite beta although the invention is not limited to the preferred zeolite. Zeolite beta is commercially available, and methods for preparing or modifying zeolite beta are disclosed, for example, in U.S. Pat. Nos. 3,308,069, 5,116,794, 5,139,759, 5,164,169, 5,164,170, 5,256,392, 5,258,570, 5,427,765, 5,457,078, 5,980,859 and 6,004,527.

The zeolites and molecular sieves of the present invention may be combined with other materials, as known in the art. For example, zeolites and molecular sieves may optionally be metal cation exchanged following the hydrogen forming cation exchange. If the zeolites and molecular sieves are metal cation exchanged after the hydrogen forming cation exchange, the zeolites or molecular sieve component thereof preferably includes a number of acid sites as hereinabove described. As representatives of metal cations, there may be mentioned cations of group IIA, group IIIA, groups IIIB to VIIB. The use of such metal cations is known in the art and the incorporation of such additional metal cations, and the amount thereof is deemed to be within the skill of the art from the teachings herein. Similarly, the zeolites or molecular sieve may be employed with one or more inorganic oxide matrix components, which is generally combined with zeolites and molecular sieves during the exchange with a metal cation if used. Such matrix components are general inorganic oxides such as silica-aluminas, clays, aluminas, silicas, etc. The matrix may be in the form of a sol, hydrogel or gel and is generally an alumina, silica or silica-alumina component such as a conventional silica-alumina catalyst. The matrix may be catalytically active or inert. In a preferred embodiment, when combined with a matrix, the zeolite component has a number of strong acid sites, as herein described.

In accordance with a further aspect of the present invention, zeolites having an improved catalytic activity may be produced by increasing the strong acid sites thereof. In this respect, during the procedures for producing zeolites, and in particular the procedure for removing the organic nitrogen templating agent, the conditions employed therein should be controlled to preserve strong acid sites. In this respect, strong acid sites are maintained by employing process conditions which prevent loss of those sites that are proven to be beneficial in catalytic conversion applications. While not wishing to be bound to any particular theory, it is believed that those sites can be ascribed to be a specific kind of tetrahedral aluminum sites in the zeolite structure.

In accordance with a preferred embodiment of the present invention, the zeolites or molecular sieve have an Acidity-Activity Index (AAI) of at least 1, preferably at least 1.2, and more preferably at least 1.4, and most preferably at least about 1.6 wherein AAI, as used in the specification and claims herein, is the ratio of the total ammonia desorbed from the zeolite or molecular sieve at a temperature above 300° C. to the total ammonia desorbed from the zeolite or molecular sieve at a temperature below 300° C., as measured by the temperature controlled desorption performed in accordance with Example 3 of U.S Pat. No. 6,809,055 B2.

In this respect, in removing the organic nitrogen templating agent (in general, at least 50% thereof is removed and in a preferred embodiment substantially all is removed), heating during calcination is controlled to prevent exposure to average temperatures of above 600° C. The calcining temperature is preferably no more than about 575° C., more preferably no more than about 550° C., and most preferably no more than about 500° C. Moreover, in a preferred embodiment, heating is carefully controlled to avoid local overheating to temperatures above about 575° C.

In a preferred embodiment of the invention, during calcining the temperature is raised gradually, for example, at a rate of no more than about 10° C./min, more preferably no more than about 5° C./min to an intermediate temperature (e.g., about 120° C.), held for a period of time at that temperature, and then gradually raised again to the calcining temperature.

In accordance with the present invention, the zeolite containing an organic template is calcined by heating to a controlled temperature in a fluidized-bed reactor.

Referring now to FIG. 1, a fluidized-bed reactor 100 suitable for use in the invention includes a generally tubular vessel 101 having an upper outlet 102 and a bottom inlet 103. In a preferred embodiment the tubular vessel can be fabricated from quartz or other high temperature material (e.g., metals or ceramics). A porous fritted disk 104 is disposed across the inner diameter of the vessel 101 in the vicinity of the bottom inlet 103 for supporting a bed of catalyst particles 10. The porous disk can be fabricated from quartz, ceramic, metal, or other suitable material.

Vessel 101 can be supported by a tripod 105, or any other suitable means. A conduit 106 has a conduit inlet 107 and extends to the bottom inlet 103 of vessel 101. Conduit 106 communicates gas of a controlled temperature to the interior of vessel 101. The hot gas passes through the porous disk into bed of catalyst particles at such a velocity that the catalyst particles become fluidized. Typically, gas velocity can range from about 50 ml/min to about 2,000 ml/min, depending on, for example, the size and density of the fluidized particles.

The gas used to fluidize the catalyst bed generally contains at least some oxygen and can be, for example, air or a mixture of an inert gas (e.g., nitrogen, helium, argon, etc.)

with oxygen, wherein the oxygen concentration of the mixture is up to about 28% by volume.

As hereinabove described, in order to maintain strong acid sites, the processing conditions should be controlled to avoid exposing the zeolite or molecular sieve to elevated temperatures for a prolonged period of time.

The zeolites and molecular sieves of the present invention may be employed for catalytically converting a feedstock wherein the zeolites or molecular sieve forms all or a portion of a catalyst in a reaction zone. A feedstock is introduced into the reaction zone for contact with the catalyst under conditions effective to convert the feedstock into a desired product.

The amount of zeolite or molecular sieve catalyst in the reaction zone may vary over a wide range depending, for example, on the specific processing application involved. A particularly suitable process is aromatic alkylation such as the alkylation of benzene with ethylene to produce ethylbenzene or the alkylation of benzene with propylene to produce cumene.

The aromatic alkylation process may be carried out in a batch, semi-continuous, or continuous fashion. The processes can be conducted in a single reaction zone or a number of reaction zones arranged in series or in parallel, or they may be conducted intermittently or continuously in an elongated tubular zone or a number of such zones. When multiple reaction zones are employed, it may be advantageous to employ one or more of such zeolite catalyst compositions in series to provide for a desired product mixture. Owing to the nature of the hydrocarbon conversion process, it may be desirous to carry out the certain processes by use of the zeolite catalyst compositions in a dynamic (e.g., fluidized or moving) bed system or any system of a variety of transport beds rather than in a fixed bed system. Such systems would readily provide for any regeneration (if required) of the zeolite beta catalyst compositions after a given period of time. If regeneration is required, the zeolite beta catalyst compositions can be continuously introduced as a moving bed to a regeneration zone where they can be regenerated, such as for example by removing carbonaceous materials by oxidation in an oxygen-containing atmosphere. In the preferred practice of some hydrocarbon conversion processes, the zeolite beta catalyst compositions will be subject to a regeneration step by burning off carbonaceous deposits accumulated during reactions.

The invention will be further described with respect to the following examples. However, the scope of the invention is not limited thereby. Unless otherwise indicated all parts and percentages are by weight.

In order to demonstrate the invention in the following examples, a laboratory scale fluidized-bed apparatus 100 as shown in FIG. 1 was employed to treat the catalyst to remove the organic template. The vessel 101 was fabricated from quartz tubing having a 25.4 mm outer diameter and a 18.0 mm inner diameter. The lengthwise dimension H-1 from the top of the vessel 101 at outlet 102 to the position of the porous disk 104 was 175 mm. The length H-2 from the porous disk 104 to the bottom inlet 103 was 40 mm. The legs of the tripod support 105 had a length H-3 of 47 mm. The conduit 106 was fabricated from a 6 mm outer diameter quartz tube. Length H-4 of conduit 106 was 500 mm.

The conduit 106 was supported by quartz rod 108 which was fixed at one end to vessel 101.

The fluidized-bed reactor 100 was placed in a furnace which was heated to the temperature indicated in the Examples.

The top opening 107 of the conduit 106 protruded from a small opening in the top of the furnace and was connected to valves, flow meter and/or flow controllers, and a source of air or oxygen/nitrogen mixture for gas flow through the catalyst fluidized-bed.

Temperature Programmed Ammonia Desorption, "Ammonia TPD", was used to measure strong acidity sites in the catalyst and was carried out in a micro-reactor/mass spectrometer unit, an online analysis system combining a quartz micro-reactor and a quadrupole mass spectrometer (Hiden Analytical HPR-20).

About 40 mg powder sample was used, and the final result was corrected to a dry basis after moisture has been taken into account. The sample was first calcined in air with a flow rate of 50 ml/min at 400° C. for 30 minutes and then cooled down to 125° C. in 50 ml/min flowing He and held for 10 minutes. Ammonia adsorption was carried out at 125° C. in a gas mixture of 1.0% $NH_3$ in He with a flow rate of 50 ml/min for 30–35 minutes. Then, the sample was purged with 50 ml/min He at 125° C. for 4 hours. The weakly adsorbed ammonia, which is a function of adsorption temperature, time and ammonia concentration, was almost completely removed. Ammonia TPD starts from 125 to 700° C. at a heating rate of 10° C./min and a He flow rate of 50 ml/min. Mass number 16 was used for quantification to eliminate any interference from water signal. Immediately after each TPD run, quantification of ammonia desorption was based on the calibration of the mass spectrometer with 1.0% $NH_3$. As measured by ammonia TPD, zeolite treated in accordance with the invention has a strong acidity of at least about 0.55 $NH_3$ mmol/g, more preferably at least about 0.60 $NH_3$ mmol/g, and most preferably at least about 0.65 $NH_3$ mmol/g.

Surface area, pore volume, and pore diameter of the catalyst samples were measured by standard measurement techniques.

Zeolite beta samples were obtained commercially from Zeolyst International Co. of Valley Forge, Pa.

Virtually any hydrocarbon-conversion process which is capable of being catalyzed by a zeolite or molecular sieve catalyst composition could benefit from this invention. Illustrative exemplification of the present invention can be shown for aromatic alkylation. Two industrially important aromatic alkylation processes are the production of ethylbenzene and the production of cumene. Catalyst alkylation activity was tested in one or both of the following reactions.

I. Benzene alkylation with ethylene to form ethylbenzene.

The catalytic activity of the zeolite catalysts were evaluated in the model reaction of benzene alkylation with ethylene to form ethylbenzene. The test reactor was a recirculating differential fixed bed reactor. The test conditions were a pressure of 350 psig and a temperature of 190° C., and the recirculation rate was 200 grams/min. The test feed contained 0.35 wt. % ethylene dissolved in benzene with a feed rate of 6.0 grams/min.

The catalyst charge was 1.0 gram with a particle size of −12 to +12 mesh, derived from 1.6 mm extrudates containing 80 wt % zeolite. The test was carried out for 7 to 8 hours with samples taken every 30 minutes for analysis by gas chromatography ("GC"). The first-order reaction rate constant, $k_{EB}$, was calculated at 190° C. to represent catalyst activity for the alkylation of benzene with ethylene to produce ethylbenzene. Zeolite treated in accordance with the method of the invention typically has a $k_{EB}$ (at 190° C.) of at least about 0.75, preferably at least about 1.0, and more preferably at least about 1.6.

II. Benzene alkylation with propylene to form cumene.

This reaction was conducted in a manner similar to that of benzene alkylation with ethylene and with the same test equipment except that the feed contained 0.35% wt % propylene dissolved in benzene and the reaction temperature was 170° C. The first-order reaction rate constant, $k_{CU}$, was calculated at 170° C. to represent catalyst activity for the alkylation of benzene with propylene to produce cumene. Zeolite treated in accordance with the method of the invention typically has a $k_{CU}$ (at 170° C.) of at least about 5.0, preferably at least about 6.0, and more preferably at least about 7.0.

EXAMPLE 1

Zeolite beta crystals which still contained some organic templating agent were loaded into the fluidized-bed reactor was described above. The reactor was placed inside a Fisher Precision furnace and a gas mixture containing 5% oxygen and 95% nitrogen was made to flow through the bed of zeolite at a rate of 480 ml/min, which was sufficient to fluidize the bed. For calcination of the zeolite the temperature of the fluidized-bed was raised at 1° C. per minute to 120° C., held for 1 hour, then raised again at 1° C. minute to 550° C., held for 10 hours, and finally cooled at the rate of 5° C./min to room temperature. The resulting calcined zeolite was then ion exchanged in a 0.1 Molar aqueous solution of ammonium nitrate at room temperature. After filtration and washing the ion exchanged sample was dried at 120° C.

The dried ion exchanged zeolite powder was then mixed with appropriate amount of Nyacol® alumina sol so that the final calcined product contains a zeolite concentration of about 80 wt %. The paste was dried at 90° C. for 1 hr and then calcined with the following program: 5° C./min to 120° C., held for 1 hr, 5° C./min to 500° C., held for 5 hr, 5° C./min to room temperature. The calcined pastes were crushed and sieved to +20/−12 mesh size, of which 0.76 gram, designated as Sample 1, was loaded into the alkylation reactor for performance evaluation.

The test results of Sample 1 are set forth below as follows:

Sample 1

Catalyst activity, $k_{EB}$ @ 190° C. (cm³/g.s) 1.94

EXAMPLE 2

Zeolite beta crystals which still contained some organic templating agent were loaded into the fluidized-bed reactor and calcined in the same manner as in EXAMPLE 1 except that air was used as the fluidizing gas, and the temperature was ramped up at the rate of 5° C./min to 120° C., held for 1 hour, then heated again at the rate of 5° C./min to a temperature of 550° C., held for 3 hours, then cooled at 5° C./min to room temperature.

The calcined zeolite was ion exchanged in the same manner as described in EXAMPLE 1 and formed into an extrudate with Nyacol® alumina in the same manner as described in EXAMPLE 1. The resulting catalyst, designated as Sample 2, was tested for acid sites by ammonia TPD (as described above, surface area and pore volume and both ethylbenzene alkylation activity ($k_{EB}$) and cumene alkylation activity ($k_{CU}$), and had the following characteristics:

Sample 2

| | |
|---|---|
| Strong acidity (NH₃ mmol/g) | 0.61 |
| $S_{BET}$ (m²/g) | 499 |
| Pore volume (cc/g) | 0.724 |
| Avg. Pore diameter (Å) | 107 |
| Catalyst activity $k_{EB}$ @ 190° C. (cm³/g.s) | 2.16 |
| Catalyst activity $k_{CU}$ @ 170° C. (cm³/g.s) | 8.06 |

EXAMPLE 3

Zeolite beta crystals which still contained some organic templating agent were calcined in the same manner as set forth in EXAMPLE 2. The calcined zeolite was formed into a catalyst extrudate in the same manner as set forth in EXAMPLE 2, and was designated as Sample 3 and then tested for acid sites, surface area, pore volume, pore size and ethylbenzene alkylation in the same manner as set forth in EXAMPLE 2. Sample 3 had the following characteristics.

Sample 3

| | |
|---|---|
| Strong acidity (NH₃ mmol/g) | 0.67 |
| $S_{BET}$ (m²/g) | 538 |
| Pore volume (cc/g) | 0.828 |
| Avg. Pore diameter (Å) | 113 |
| Catalyst activity $k_{EB}$ @ 190° C. (cm³/g.s) | 1.61 |

The following Comparative Examples are not in accordance with the invention.

COMPARATIVE EXAMPLE A

Zeolite beta crystals which still contained organic template were calcined in a tray calciner. The tray calciner was obtained from Padelt-Therm GmbH of Leipzig Germany under the model number REU 240-750. A layer of zeolite beta of about ⅛ inch thickness was placed on the ceramic tray of the calciner. The zeolite beta was heated from room temperature to 120° C. at a rate of 5° C./min, held for 1 hour, then heated to 550° C./min at 5° C./min, held at that temperature for 10 hours, then cooled to room temperature at the rate of 5° C./min.

The calcined zeolite was formed into a catalyst extrudate in the same manner as set forth in the Examples above. The calcined zeolite was designated as Sample 4 and then tested for acid sites, surface area, pore volume, pore size and ethylbenzene alkylation in the same manner as set forth in the Examples above. Sample 4 had the following characteristics:

Sample 4

| | |
|---|---|
| Strong acidity (NH₃ mmol/g) | 0.58 |
| $S_{BET}$ (m²/g) | 524 |
| Pore volume (cc/g) | 0.758 |
| Avg. Pore diameter (Å) | 107 |
| Catalyst activity $k_{EB}$ @ 190° C. (cm³/g.s) | 0.75 |

COMPARATIVE EXAMPLE B

Zeolite beta crystals which still contained organic templiate were calcined in the same manner as COMPARATIVE EXAMPLE A. The calcined zeolite, designated as Sample 5, was formed into a catalyst extrudate in the same manner as set forth in the Examples set forth above, and was tested for both ethylbenzene alkylation and cumene alkylation activity. Sample 5 had the following characteristics:

Sample 5

| | |
|---|---|
| Catalyst activity, $k_{EB}$ @ 190° C. (cm³/g.s) | 0.80 |
| Catalyst activity, $k_{CU}$ @ 170° C. (cm³/g.s) | 2.48 |

COMPARATIVE EXAMPLE C

Zeolite beta crystals which still contained organic templiate were calcined in a Thermocraft 6" electric rotary calciner (Model No. 2825-108-47h) at a rotation rate 3 RPM, feed rate of 25 g/min and temperature of 1050° F. (566° C.).

The calcined zeolite was formed into a catalyst extrudate in the same manner as in the Examples above and designated as Sample 6, and was tested for ethylbenzne alkylation activity. Sample 6 had the following characteristic.

Sample 6

| | |
|---|---|
| Catalyst activity, $k_{EB}$ @ 190° C. (cm³/g.s) | 0.81 |

COMPARATIVE EXAMPLE D

A sample of already calcined zeolite beta obtained commercially was tested for acid sites, surface area, pore volume and pore size in the same manner as the Examples given above. The zeolite was formed into catalyst extrudates in the same manner as the Examples and designated as Sample 7, and was tested for ethylbenzene alkylation activity. Sample 7 had the following characteristics:

Sample 7

| | |
|---|---|
| Strong acidity (NH₃ mmol/g) | 0.36 |
| $S_{BET}$ (m²/g) | 466 |
| Pore volume (cc/g) | 0.491 |
| Avg. Pore diameter (Å) | 75 |
| Catalyst activity $k_{EB}$ @ 190° C. (cm³/g.s) | 0.34 |

COMPARATIVE EXAMPLE E

The same commercial zeolite beta as in COMPARATIVE EXAMPLE D was formed into a catalyst extrudate and designated as Sample 8, and was tested for cumene alkylation activity. Sample 8 had the following characteristic:

Sample 8

| | |
|---|---|
| Catalyst activity, $k_{cu}$ @ 170° C. (cm³/g.s) | 1.43 |

These results show that the method of the present invention employing a fluidized bed to calcine the catalyst provides a far superior catalyst having at least twice the catalytic activity for ethylbenzene alkylation as opposed to calcining methods employing tray or rotary calciners. For example, EXAMPLES 1, 2 and 3 exhibit $k_{EB}$ values (at 190° C.) of 1.94, 2.16, and 1.61, respectively, whereas COMPARATIVE EXAMPLES A, B and C had $k_{EB}$ values (at 190° C.) of 0.75, 0.80 and 0.81 respectively. The commercial zeolite beta of COMPARATIVE EXAMPLE D had a $k_{EB}$ value (at 190° C.) of only 0.34. Similarly, Sample 2 of EXAMPLE 2 had a $k_{CU}$ (at 170° C.) of 8.06 as compared with 2.48 for COMPARATIVE EXAMPLE B and 1.43 for COMPARATIVE EXAMPLE E.

Moreover, Samples 2 and 3 of the present invention exhibited stronger acidity as measured by ammonia TPD than that of commercial zeolite beta.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A zeolite having an AAI of at least 1.2 prepared by a process including the removal of a tetraethylammonium templating agent wherein said process comprises the calcining of the zeolite at a temperature of no greater than 550° C. in a fluidized bed unit under temperature control conditions wherein after removal of the tetraethylammonium templating agent the zeolite has an AAI of at least 1.2, wherein said zeolite is selected from the group consisting of zeolite beta, TEA-mordenite and TEA-ZSM-12.

\* \* \* \* \*